(12) United States Patent
Hernàndez Gallego et al.

(10) Patent No.: US 9,365,544 B2
(45) Date of Patent: Jun. 14, 2016

(54) PROCESS FOR THE PREPARATION OF INTERMEDIATES FOR THE SYNTHESIS OF DABIGATRAN ETEXILATE, AND CRYSTALLINE FORMS OF SAID INTERMEDIATES

(71) Applicant: INTERQUIM, S.A., Sant Cugat del Vallès (ES)

(72) Inventors: Santos Hernàndez Gallego, Cerdanyola del Vallès (ES); Francisco Marquillas Olondriz, Barcelona (ES); Marta Pomares Marco, Sant Cugat del Vallès (ES)

(73) Assignee: INTERQUIM, S.A., Sant Cugat del Valles (ES)

( * ) Notice: Subject to any disclaimer, the term of this patent is extended or adjusted under 35 U.S.C. 154(b) by 0 days.

(21) Appl. No.: 14/415,093

(22) PCT Filed: Jul. 15, 2013

(86) PCT No.: PCT/EP2013/064884
§ 371 (c)(1),
(2) Date: Jan. 15, 2015

(87) PCT Pub. No.: WO2014/012880
PCT Pub. Date: Jan. 23, 2014

(65) Prior Publication Data
US 2015/0203470 A1    Jul. 23, 2015

Related U.S. Application Data

(60) Provisional application No. 61/747,626, filed on Dec. 31, 2012.

(30) Foreign Application Priority Data

Jul. 16, 2012 (ES) .................................. 201231112

(51) Int. Cl.
*C07D 401/12* (2006.01)

(52) U.S. Cl.
CPC .................................. *C07D 401/12* (2013.01)

(58) Field of Classification Search
CPC ....................................................... C07D 401/12
USPC ....................................................... 546/273.4
See application file for complete search history.

(56) References Cited

U.S. PATENT DOCUMENTS 8,119,810 B2 *    2/2012    Broeder ............... C07D 401/12
                                                          546/273.4

OTHER PUBLICATIONS

Lin et al., "Synthesis of an achiral, etc.," CA 146:27828 (2006).*
Anon., "Intermediates for the, etc.," CA 159:624603 (2012).*

* cited by examiner

*Primary Examiner* — Patricia L Morris
(74) *Attorney, Agent, or Firm* — Birch, Stewart, Kolasch & Birch, LLP (57) ABSTRACT

The present invention relates to new processes for the preparation of synthesis intermediate products useful in the preparation of Dabigatran Etexilate on an industrial scale. The invention also relates to new crystalline forms of intermediate products thus obtained.

10 Claims, 2 Drawing Sheets

PROCESS FOR THE PREPARATION OF INTERMEDIATES FOR THE SYNTHESIS OF DABIGATRAN ETEXILATE, AND CRYSTALLINE FORMS OF SAID INTERMEDIATES

CROSS REFERENCE TO RELATED APPLICATIONS

This application is the National Phase of PCT/EP2013/064884 filed on Jul. 15, 2013, which claims priority under 35 U.S.C. 119(e) to U.S. Provisional Application No. 61/747,626, filed on Dec. 31, 2012 and under 35 U.S.C. 119(a) to Patent Application No. 201231112, filed in Spain on Jul. 16, 2012, all of which are hereby expressly incorporated by reference into the present application.

FIELD OF THE ART

The present invention relates to new processes for the preparation of synthesis intermediate products useful in the preparation of Dabigatran Etexilate. The invention also relates to new crystalline forms of intermediate thus obtained.

BACKGROUND ART

Dabigatran Etexilate of formula (V), which chemically corresponds to the ethyl (E) 3-(2-((4-(N'-(hexyloxycarbonyl)carbamimidoyl)phenylamino)methyl)-1-methyl-N-(pyridin-2-yl)-1H-benzo[d]imidazole-5-carboxamido)propanoate, is an anticoagulant from the class of direct thrombin inhibitors and is used for the treatment of thrombosis, cardiovascular diseases and similar diseases:

The active ingredient was first described in the patent application WO98/37075. In said document, a process for obtaining Dabigatran Etexilate according to the following route of synthesis is described:

-continued

Amidine hydrochloride (IV-HCl)

Dabigatran etexilate (V)

In this process are required purification by chromatography in several of its steps, in particular, in the steps of obtaining the compound (III) and the amidine hydrochloride salt of formula (IV-HCl), which affects in a particularly disadvantageous way in the preparation of the compound of formula (V) on an industrial scale.

The first step corresponds to the preparation of the free base of the compound (III) by reacting the carboxylic acid (I) with the diamine (II) in the presence of a suitable coupling reagent. The reaction is carried out in tetrahydrofuran. The product obtained (III) requires a purification by chromatography, which is very difficult and costly to implement on an industrial scale.

In a next step the cyano derivative (III) is reacted with a dissolution of hydrogen chloride in ethanol, followed by the addition of ammonium carbonate in ethanol to give rise to the amidine hydrochloride salt (IV-HCl). Also in this case, it is required a purification by chromatography of the synthesis intermediate (IV-HCl).

The last step corresponds to the reaction of the intermediate (IV-HCl) with hexyl chloroformate to form the active pharmaceutical ingredient Dabigatran Etexilate.

In order to simplify the process for obtaining Dabigatran Etexilate described in WO98/37075, expensive and difficult to carry out on a large scale industry, several alternative processes have been developed.

In the patent application EP2262771A1 the compound of formula (III) is obtained in form of a salt with oxalic acid. This document indicates that the oxalate intermediate of the compound of formula (III) crystallizes easily and is a good synthesis intermediate to obtain the amidine hydrochloride salt of formula (IV-HCl) with high purity on an industrial scale. The compound of formula (III) in the form of oxalate is transformed in Dabigatran following the process of WO98/37075.

The patent EP2118090B1 protects a process for the preparation on an industrial scale of an synthesis intermediate product in the preparation of Dabigatran Etexilate, in particular, the amidine of formula (IV-pTsOH) which is isolated from the reaction medium by crystallization from a salt with p-toluenesulfonic acid. This amidine salt (IV-pTsOH) is obtained from a compound of formula (III) which is also isolated in form of a salt, in this case hydrobromide (III-HBr). Said patent explains that this salt (III-HBr) can be easily isolated, which significantly simplifies the process of preparation of this intermediate product in the case of reactions on an industrial scale.

The document WO2012/004396 explains that, following the processes described so far in the state of the art such as for example in WO98/37075, the step of preparation of the amidine of formula (IV) is particularly complicated. This step requires the use of large amounts of ammonia or ammonium carbonate required for the conversion of the compound of formula (III) into the amidine of formula (IV) and also to neutralize the large amount of acid still in dissolution. As a result, the process generates large amounts of residual salts in form of ammonium chloride. These secondary reaction products greatly complicate the process, especially on an industrial scale where chromatographies cannot be carried out. WO2012/004396 intends to solve said problem through the isolation of the imidate intermediate (VI) which is formed after the reaction of the compound of formula (III) with hydrogen chloride in ethanol:

(VI)

In the bibliographic article "Intermediates of N-(2-(4-(N-Hexyloxycarbonyl)amidino)phenylaminomethyl)-1-methyl-1H-benzimidazol-5-ylcarbonyl)-(2-pyridil)beta-alanine ethyl ester" (*IP.com Journal*, 2009, vol. 9(3A), pp. 20; IPCOM000179673D) it is described a process for the preparation of the amidine hydrochloride salt of formula (IV-HCl) by reaction of the compound (III) with hydrogen chloride in ethanol, followed by a neutralization of anhydrous reaction medium with ammonium carbonate, inevitably generating, as in WO98/37075, huge amounts of ammonium chloride salts difficult to separate from the reaction mixture. Alternatively to the purification by chromatography proposed in WO98/37075, in this publication the purification step of the amidine hydrochloride salt (IV-HCl) consists of hot dissolving the crude reaction product in isopropanol and filtering while it is hot to remove the ammonium chloride salts. In a disadvantageous way, the same operation must be repeated several times to remove all salts and isolate the pure amidine hydrochloride salt (IV-HCl), resulting in a yield of the process of only 41%.

In document WO2010/045900, in the same way that in the document EP2262771A1 mentioned above, the amidine hydrochloride salt of formula (IV-HCl) is prepared from the oxalate salt of the compound of formula (III) by reacting with hydrogen chloride in ethanol, followed by reaction with ammonium carbonate in anhydrous. As described in WO2010/045900, the use of the oxalate salt of the compound of formula (III) as a starting material, allowed them to solve the problems encountered in the process proposed in WO98/37075. The inventors of WO2010/045900 reproduced the process according to WO98/37075 obtaining the amidine of formula (IV-HCl) in form of an oily substance with a high content of impurities, which had to be purified by chromatography as indicated in WO98/37075, since they failed to find any solvent for purifying the amidine by simple crystallization. For this reason, the inventors of WO2010/045900 sought other alternative process, in particular, through the oxalate salt of the compound of formula (III) to avoid a chromatography technically impossible to carry out on a large scale industrial.

In view of the foregoing, it is of great interest to continue investigating and develop other alternative simplified processes for the large scale industrial production of the active pharmaceutical ingredient Dabigatran Etexilate or salts thereof, avoiding purifications very complicated and costly in each step of preparation of synthesis intermediates, while maintaining a high quality of synthesis intermediates and improving yields of each step of reaction.

EXPLANATION OF THE INVENTION

Surprisingly, the inventors have found that by modifying certain parameters of reaction and solvents in the route of synthesis of Dabigatran Etexilate described in document WO98/37075, some of the synthesis intermediates can be prepared in a large scale, with good yield and purity, in particular, the compound of formula (III)

(III)

and the amidine hydrochloride salt of formula (IV-HCl)

(IV-HCl)

On the other hand, the inventors have also found new crystalline forms of the compound of formula (III) and amidine hydrochloride salt of formula (IV-HCl). The isolation of these synthesis intermediates in crystalline form is very advantageous, especially on an industrial scale, and contributes to obtaining the final product Dabigatran Etexilate with high yield and purity.

According to the present invention, the active pharmaceutical ingredient Dabigatran Etexilate, or a salt thereof such as Dabigatran Etexilate mesylate, it can be prepared on an industrial scale by the following route of synthesis:

Thus, the present invention describes a process for producing on an industrial scale the amidine hydrochloride salt of formula (IV-HCl)

characterized in that the compound of formula (III) in free base form is reacted with hydrogen chloride in the presence of an alcohol, and then with ammonia in an aqueous medium to form the amidine hydrochloride salt of formula (IV-HCl) in the presence of water.

The crucial point of the present step resides in adding water to finish the reaction with ammonia in aqueous medium, and distilling alcohol from the reaction mixture. In this way, two liquid phases are then formed and when the mixture is heated between 35° C. and 50° C., a white solid precipitates. After cooling between 0° C. and 5° C. the hydrochloride salt of formula (IV-HCl) is isolated by simple filtration with good purity (above 90% measured by HPLC) and with a yield higher than 85%.

It is known from the state of the art that the step of preparation of the amidine hydrochloride salt of formula (IV-HCl) from of the compound of formula (III) tends to be particularly difficult, since it requires the use of large amounts of ammonia or ammonium carbonate to neutralize the excess of acid required in the reaction. Excess of these reagents has resulted in the formation of large amounts of ammonium chloride salts which are difficult to separate from the reaction mixture.

Surprisingly, by means of a change of reaction parameters according to the present invention, it is achieved advantageously the isolation of the hydrochloride salt of the compound (IV-HCl) by simple precipitation in an aqueous medium with high yield and purity. Unexpectedly, it was noted that when more water was added after the reaction with aqueous ammonia to neutralize the excess of acid in the reaction mixture, it is achieved the dilution of the ammonium chloride salts and the precipitation of the hydrochloride salt (IV-HCl) in water. Thus, the process for the preparation of the hydrochloride salt (IV-HCl) is drastically simplified compared to the processes in the state of the art, since for example the need to perform a purification of the final product by repeated hot filtrations, or by chromatography, is avoided.

This result is surprising, especially in light of the document WO2010/045900 wherein it is explained that no solvent was not found to precipitate the hydrochloride salt of the product (IV-HCl) and avoid a chromatography. No documents in the state of the art suggest these reaction conditions and other alternative processes are proposed, such as for example in WO2010/04900 wherein it is described the use of the oxalate salt of the product (III) as a starting material instead of the free base of the compound (III). The process of the present invention drastically simplifies the preparation of the amidine hydrochloride salt of formula (IV-HCl), easily separating the excess of residual salts formed during the reaction.

The reaction with hydrogen chloride occurs in an alcohol, preferably ethanol, at room temperature (between 15° C. and 25° C.). Preferably, it is used between 15 and 25 equivalents of a dissolution of saturated hydrogen chloride in alcohol. After the reaction with hydrogen chloride, alcohol is added, preferably ethanol, and then a dissolution of aqueous ammonia, preferably of 25%, up to a pH value of between 8.5 and 9.5 to neutralize the excess of acid present in the reaction mixture.

After the neutralization of the reaction medium, water is added and the alcohol is distilled. Preferably, it is used between 130 and 540 equivalents of water. More preferably, it is used between 175 and 280 equivalents of water.

The solid (IV-HCl) obtained by simple filtration, following the reaction conditions of the process of the present invention is a crystalline compound with a defined structure of a purity higher than 90% (HPLC).

In a preferred embodiment of the present invention, the crude product of the compound of formula (IV-HCl) is recrystallized from a subsequent purification step in a isopropanol/water mixture. Preferably, it is used a proportion by volume of isopropanol/water comprised between 11:1 and 16:1.

In this purification step, the suspension of the crude product (IV-HCl) is heated in the isopropanol/water mixture at 75-85° C. until obtaining a dissolution. It is allowed to cool up to room temperature and then the mixture is cooled at 0-5° C.

In this way it is obtained a crystalline compound with a high yield between 80% and 90%, and a HPLC purity higher than 99% free of the ammonium chloride salts. This purified solid of the compound (IV-HCl) has the same crystalline form as the crude solid of the compound (IV-HCl) directly obtained after the reaction.

Thus, the present invention also relates to a new crystalline form of the compound of formula (IV-HCl) ethyl 3-(2-((4-carbamimidoylphenylamino)methyl)-1-methyl-N-(pyridin-2-yl)-1H-benzo[d]imidazole-5-carboxamido)propanoate hydrochloride in anhydrous crystalline form, obtainable by the process as defined above with or without purification in an isopropanol/water mixture.

Figure 3:
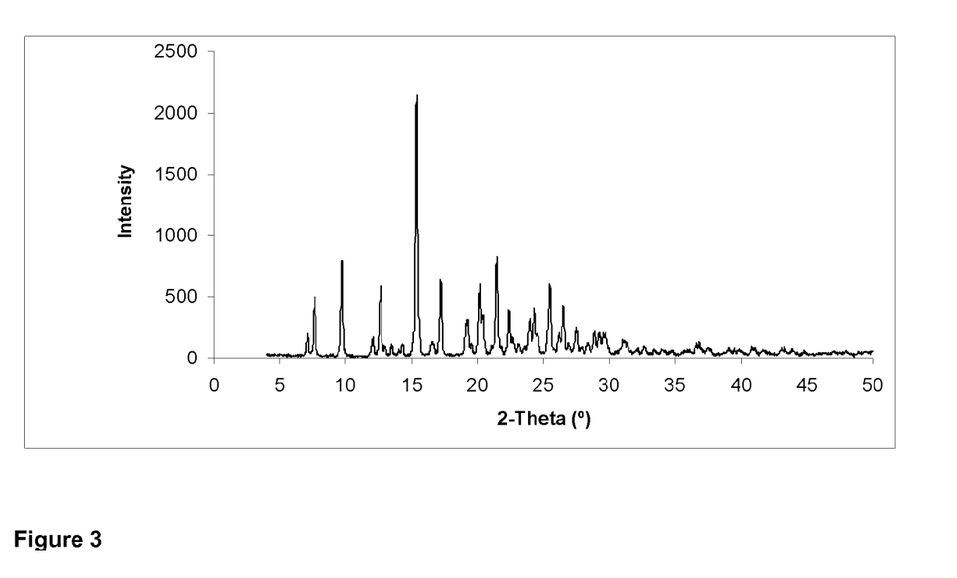
FIG. 3 depicts the x-ray diffractogram with Cu K alpha radiation (1.5418 Å) a new crystalline form of the compound of formula (IV-HCl), that is, of the compound ethyl 3-(2-((4-carbamimidoylphenylamino)methyl)-1-methyl-N-(pyridin-2-yl)-1H-benzo[d]imidazole-5-carboxamido)propanoate hydrochloride in anhydrous crystalline form.

Likewise, the present invention also relates to a new crystalline form of the compound of formula (IV-HCl) ethyl 3-(2-((4-carbamimidoylphenylamino)methyl)-1-methyl-N-(pyridin-2-yl)-1H-benzo[d]imidazole-5-carboxamido) propanoate hydrochloride in anhydrous crystalline form, characterized in that it has x-ray diffraction peaks (angle 2-theta values (°)): 7.7; 9.7; 12.6, and 15.4 measured on a x-ray diffractometer with Cu K alpha radiation (1.5418 Å). In particular, this compound shows an x-ray diffractogram that essentially corresponds to that of FIG. 3.

Likewise, the present invention also relates to a new crystalline form of the compound of formula (IV-HCl) ethyl 3-(2-((4-carbamimidoylphenylamino)methyl)-1-methyl-N-(pyridin-2-yl)-1H-benzo[d]imidazole-5-carboxamido) propanoate hydrochloride in anhydrous crystalline form, characterized in that it also has a melting point of 210-214° C. measured by differential scanning calorimetry technique (DSC).

In another preferred embodiment of the process of the invention it is carried out a purification of the product (IV-HCl) directly obtained after the reaction, or the product (IV-HCl) purified in isopropanol/water where, in a first step, the amidine hydrochloride salt of formula (IV-HCl) of anhydrous crystalline form is dissolved in water at room temperature. Surprisingly, shortly after it can be seen an abundant precipitate. It is stirred at 55-60° C. for 30 minutes and then the mixture is cooled at 0-5° C. Thus, the amidine hydrochloride salt of formula (IV-HCl) is easily isolated as a well filterable new dihydrate crystalline form. The crystalline form of the amidine hydrochloride salt of formula (IV-HCl) in the dihydrate form has a purity higher than 99% measured by HPLC.

Thus, the present invention also relates to a new crystalline form of the compound of formula (IV-HCl) ethyl 3-(2-((4-carbamimidoylphenylamino)methyl)-1-methyl-N-(pyridin-2-yl)-1H-benzo[d]imidazole-5-carboxamido)propanoate hydrochloride dihydrate in crystalline form, obtainable by the process including an additional purification step in water defined above.

Figure 4:
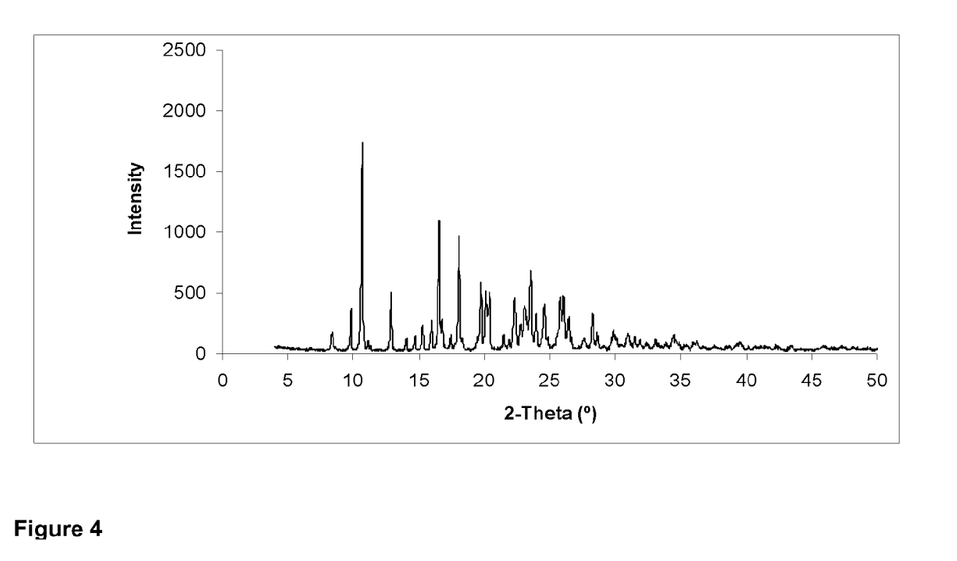
FIG. 4 depicts the x-ray diffractogram with Cu K alpha radiation (1.5418 Å) a new crystalline form of the compound of formula (IV-HCl), that is, of the compound ethyl 3-(2-((4-carbamimidoylphenylamino)methyl)-1-methyl-N-(pyridin-2-yl)-1H-benzo[d]imidazole-5-carboxamido)propanoate hydrochloride dihydrate in crystalline form.

Likewise, the present invention relates to a new crystalline form of the compound of formula (IV-HCl) ethyl 3-(2-((4-carbamimidoylphenylamino)methyl)-1-methyl-N-(pyridin-2-yl)-1H-benzo[d]imidazole-5-carboxamido)propanoate hydrochloride dihydrate in crystalline form, characterized in that it has the following x-ray diffraction peaks (angle 2-theta values (°)):10.6; 16.5, and 18.0 measured on a x-ray diffractometer with Cu K alpha radiation (1.5418 Å). In particular, this compound shows an x-ray diffractogram that essentially corresponds to that of FIG. 4.

Likewise, the present invention relates to a new crystalline form of the compound of formula (IV-HCl) ethyl 3-(2-((4-carbamimidoylphenylamino)methyl)-1-methyl-N-(pyridin-2-yl)-1H-benzo[d]imidazole-5-carboxamido)propanoate hydrochloride dihydrate in crystalline form, characterized in that it also has a melting point of 210-214° C. measured by differential scanning calorimetry technique (DSC).

Finally, in a last step, the amidine hydrochloride salt of formula (IV-HCl) obtained is converted in Dabigatran Etexilate of formula (V), or a salt thereof by reacting with hexyl chloroformate, such as for example according to the process of the document WO98/37075.

In a preferred embodiment of the present invention, the present invention also relates to the process defined above characterized in that in a step prior to the formation of the amidine hydrochloride salt (IV-HCl) is reacted a diamine of formula (II)

with the carboxylic acid of formula (I)

in the presence of a coupling reagent and a solvent selected from the group consisting of isopropyl acetate, ethyl acetate, and butyl acetate;
and subsequent reaction in the presence of acetic acid to prepare the compound of formula (III)

In the process for obtaining the compound (III) of the present invention, preferably the carboxylic acid of formula (I) is first reacted with the coupling agent in a solvent selected from the group consisting of isopropyl acetate, ethyl acetate, and butyl acetate.

As appropriate coupling reagents should be mentioned, by way of example and preferably, N,N'-dicyclohexylcarbodiimide, N,N'-carbonyldiimidazole, and carbonyl-di-(1,2,4-triazole), and more preferably N,N'-carbonyldiimidazole. As reaction solvent is especially preferred isopropyl acetate.

Following the reaction of the carboxylic acid of formula (I) with the diamine of formula (II) under the above-mentioned conditions, acetic acid is added, preferably from 3 to 9 equivalents of acetic acid with regard to the carboxylic acid (I), and more preferably 6 equivalents, and the mixture is heated at a temperature comprised between 75° C. and 130° C. Subsequently the compound of formula (III) is isolated by adding water to the reaction mixture at room temperature. The washings of the organic phase are conducted and finally it is carried out an adjustment of pH between 10 and 11 forming a suspension containing the compound of formula (III).

In a preferred embodiment, this solid can be recrystallized, preferably from ethanol, thus obtaining a crystalline solid of a defined structure with a purity of 99% measured by HPLC. Thus, a synthesis intermediate with a very high purity by simple filtration is achieved, instead of using an expensive purification by chromatography.

Advantageously, the preparation of the compound of formula (III) according to the process of the invention can be carried out using a single reaction solvent. In the documents of the state of the art such as EP2118090B1, processes for coupling of the carboxylic acid (I) with the diamine of formula (II) in tetrahydrofuran are described. Prior to the addition of acetic acid, it is necessary to distil the solvent from the reaction mixture to reach a temperature that allows the formation of the compound (III). In contrast to the processes of the state of the art, in the case of the present invention the reaction between the carboxylic acid (I) and the diamine (II) is carried out in a solvent with a boiling point higher than the temperature required for the obtaining of the compound of formula (III), comprised between 75° C. and 130° C., which avoids having to distill large amounts of solvent before the addition of acetic acid. The fact of eliminating the distillation of the solvent in this step significantly simplifies the process on an industrial scale.

In addition, another advantage of the process proposed in the present invention lies in the possibility of isolating the free base of the compound (III) by a simple filtration instead of using a costly purification by chromatography.

In the present invention, the second step of the reaction with acetic acid is carried out in the same solvent already used in the first step corresponding to the coupling of the carboxylic acid (I) with the diamine (II). Thus, advantageously only it is added a minimum amount of acetic acid, adjusted to the amount necessary to form the benzimidazole ring, and thus achieving the compound (III). In this way, when working with a water non-miscible solvent and a little amount of acetic acid, an aqueous work-up can be performed directly of the reaction mixture. Through simple washings of the organic phase with water and a last adjustment of pH of reaction mixture to a value between 10 and 11, the free base of the compound (III) precipitates which can be isolated by a simple filtration. Instead, on the state of the art such as in WO98/37075, once distilled the tetrahydrofuran used in the reaction of acid (I) with the diamine (II), the process continues only in the presence of acetic acid, which serves both as reagent and solvent. In this way, it is not possible to obtain the compound of formula (III) performing a simple aqueous work-up from the reaction mixture, but the product must be isolated by chromatography.

In this way, the reaction yields of the step are also improved. The inventors were able to prepare and isolate the free base of the compound (III) by simple filtration with a yield of the crude product higher than 90% and a purity of crude product higher than 94%, while in the original patent application WO98/37075 the yield is 61% with purification by chromatography.

The inventors analyzed the solid obtained of the compound (III) prior to the recrystallization from ethanol and found a new crystalline form of the compound (III).

Thus, the present invention also relates to a new crystalline form of the compound of formula (III), that is, the compound ethyl 3-(2-((4-cyanophenylamino)methyl)-1-methyl-N-(pyridin-2-yl)-1H-benzo[d]imidazole-5-carboxamido)propanoate in crystalline form, obtainable by the process as defined above.

Figure 1:
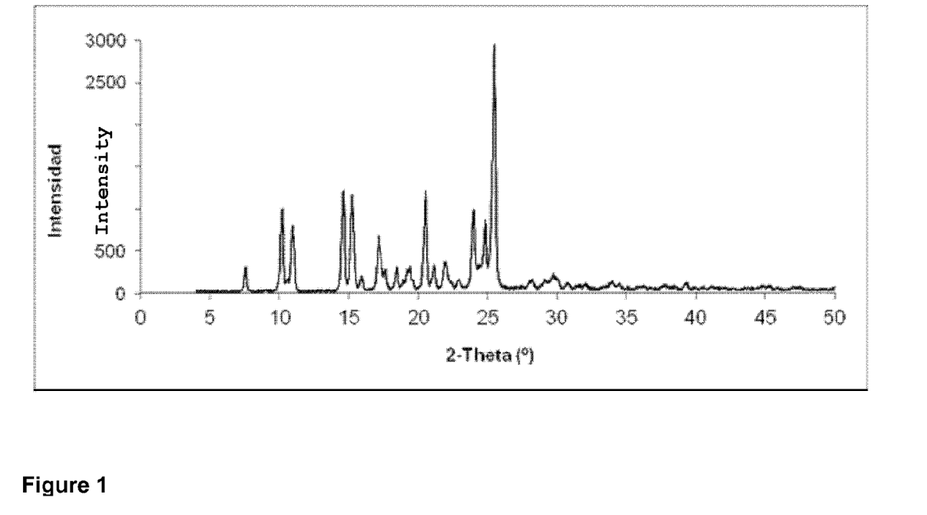
FIG. 1 depicts the x-ray diffractogram with Cu K alpha radiation (1.5418 Å) a new crystalline form of the compound of formula (III), that is, a new crystalline form of the compound ethyl 3-(2-((4-cyanophenylamino)methyl)-1-methyl-N-(pyridin-2-yl)-1H-benzo[d]imidazole-5-carboxamido) propanoate.

Likewise, the present invention relates to a new crystalline form of the compound of formula (III), that is, the compound ethyl 3-(2-((4-cyanophenylamino)methyl)-1-methyl-N-(pyridin-2-yl)-1H-benzo[d]imidazole-5-carboxamido)propanoate in crystalline form, characterized in that it has the following x-ray diffraction peaks (angle 2-theta values (°)): 7.6, 10.2, 10.9, 14.6, 15.2, 20.5, and 25.5 measured on a x-ray diffractometer with Cu K alpha radiation (1.5418 Å). In particular, this compound shows an x-ray diffractogram that essentially corresponds to that of FIG. 1.

Likewise, the present invention relates to a new crystalline form of the compound of formula (III), that is, the compound ethyl 3-(2-((4-cyanophenylamino)methyl)-1-methyl-N-(pyridin-2-yl)-1H-benzo[d]imidazole-5-carboxamido)propanoate in crystalline form, characterized in that it also has a melting point of 114-118° C. measured by differential scanning calorimetry technique (DSC).

On the other hand, the inventors also analyzed the solid obtained after the purification step in ethanol of the compound (III) and found another new crystalline form of the compound (III)

Thus, the present invention also relates to a new crystalline form of the compound of formula (III), that is, the compound ethyl 3-(2-((4-cyanophenylamino)methyl)-1-methyl-N-(pyridin-2-yl)-1H-benzo[d]imidazole-5-carboxamido)propanoate in crystalline form, obtainable by the process as defined above, including the purification step in ethanol defined above.

Figure 2:
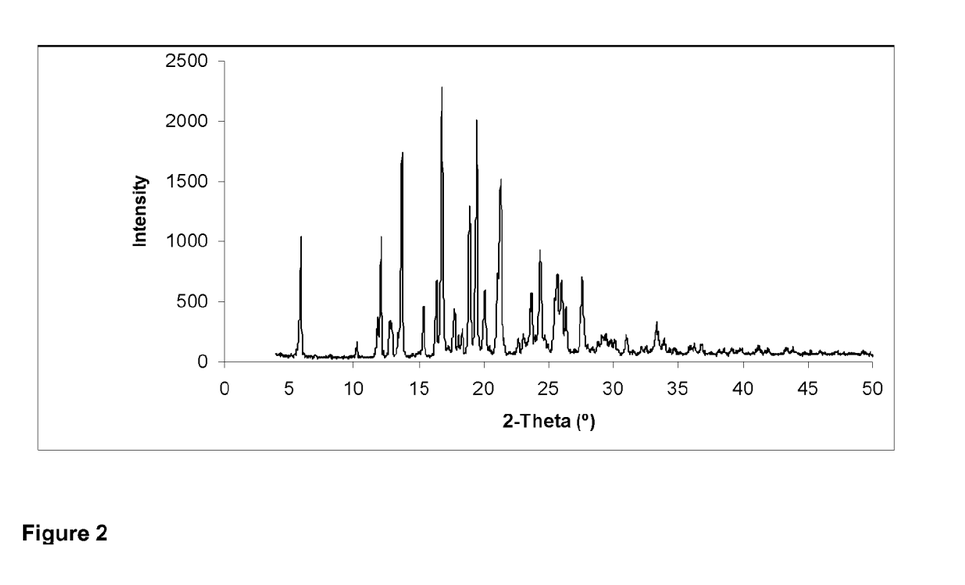
FIG. 2 depicts the x-ray diffractogram with Cu K alpha radiation (1.5418 Å) of a second new crystalline form of the compound of formula (III), that is, a new crystalline form of the compound ethyl 3-(2-((4-cyanophenylamino)methyl)-1-methyl-N-(pyridin-2-yl)-1H-benzo[d]imidazole-5-carboxamido)propanoate.

Likewise, the present invention relates to a new crystalline form of the compound of formula (III), that is, the compound ethyl 3-(2-((4-cyanophenylamino)methyl)-1-methyl-N-(pyridin-2-yl)-1H-benzo[d]imidazole-5-carboxamido)propanoate in crystalline form, characterized in that it has the following x-ray diffraction peaks (angle 2-theta values (°)): 5.9; 12.0; 13.7; 16.8, and 19.5 measured on a x-ray diffractometer with Cu K alpha radiation (1.5418 Å). In particular, this compound shows an x-ray diffractogram that essentially corresponds to that of FIG. 2.

Likewise, the present invention relates to a new crystalline form of the compound of formula (III), that is, the compound ethyl 3-(2-((4-cyanophenylamino)methyl)-1-methyl-N-(pyridin-2-yl)-1H-benzo[d]imidazole-5-carboxamido)propanoate in crystalline form, characterized in that it also has a melting point of 146-150° C. measured by differential scanning calorimetry technique (DSC).

The invention also relates to the use of compounds defined above with new crystalline forms as synthesis intermediates in a process of preparation of Dabigatran Etexilate or a salt thereof.

In conclusion, the developed process allows to easily prepare the active ingredient Dabigatran Etexilate, or a salt thereof, in particular the mesylate, on an industrial scale with high yield and purity. On the one hand, the technically costly purifications by chromatography are avoided, allowing the isolation by simple filtration of the synthesis intermediates mentioned above with high yield and purity, and on the other hand, the complications found in the state of the art regarding the difficult separation of some secondary reaction products are avoided.

EXAMPLES

The invention is explained in greater detail below through a preferred embodiment, but to which is not limited. The following examples are purely illustrative of each step of a process of synthesis carried out by way of example, and not represent a limitation of the scope of the present invention.

Example 1

Preparation of the free base ethyl 3-(2-((4-cyanophenylamino)methyl)-1-methyl-N-(pyridin-2-yl)-1H-benzo[d]imidazole-5-carboxamido)propanoate of formula (III)

Step 1: Crude Product 10.0 g of N-(4-cyanophenyl)glycine and 10.35 g of N,N'-carbonyldiimidazole (CU) are mixed at room temperature in 150 mL of isopropyl acetate. Then, 19.43 g of ethyl 3-(3-amino-4-(methylamino)-N-(pyridin-2-yl)benzamido)propanoate are added and the mixture reacts for 4 hours at room temperature. After this time, 20 mL of acetic acid are added and the mixture is refluxed for 2 hours. It is allowed to cool at room temperature and 33 mL of water are added. The organic phase is separated and further 33 mL of water are added. The pH of the mixture is adjusted to 10-11 with a dissolution of 25% of sodium hydroxide, forming a suspension. The suspension is filtered and the solid obtained is dried at 45° C. in a vacuum oven.

Yield: 24.6 g of crude base of the compound (III); (90% yield).

Product purity: 94% measured by HPLC.

Melting point: 116° C. measured by differential scanning calorimetry technique (DSC);

X-rays (angle 2-theta values (°)): 7.6, 10.2, 10.9, 14.6, 15.2, 20.5, and 25.5 measured on a x-ray diffractometer with Cu K alpha radiation (1.5418 Å).

Step 2: Purification of the Compound (III) in Free Base Form

The crude product is recrystallized from 100 mL of ethanol, and a white solid with a high purity of 99% (HPLC) is obtained.

Yield: 23.4 g of the purified base of the compound (III); (95% recrystallization yield).

Product purity: 99% measured by HPLC;

Melting point: 148° C. measured by differential scanning calorimetry technique (DSC);

X-rays (angle 2-theta values (°)): 5.9; 12.0; 13.7; 16.8; 18.9; 19.5; 21.3; 24.4, and 27.6 measured on a x-ray diffractometer with Cu K alpha radiation (1.5418 Å).

Example 2

Preparation of ethyl 3-(2-((4-carbamimidoylphenylamino)methyl)-1-methyl-N-(pyridin-2-yl)-1H-benzo[d]imidazole-5-carboxamido)propanoate hydrochloride of formula (IV-HCl)

Step 1: Crude Product 10 g of the compound (III) are mixed in 52 mL of a dissolution of saturated hydrogen chloride in ethanol at room temperature (25° C.) for 25 hours. 80 mL of ethanol are added, and then a dissolution of ammonium aqueous (25%) is added until a pH of 8.5-9.5. After 6 hours, the reaction is completed. 50 mL of water are added and the ethanol is partially distilled off. Further 25 mL of water are added and two liquid phase are formed. The mixture is heated at 35° C. and a white solid is formed. After cooling down between 0° C. and 5° C., the solid is filtered and washed with cold water. The solid is dried at 50° C. in a vacuum oven.

Yield: 9.66 g (dry weight) of the amidine hydrochloride salt of formula (IV-HCl) in anhydrous crystalline form; (87% yield).

Product purity: 92% measured by HPLC.

Step 2: Purification of ethyl 3-(2-((4-carbamimidoylphenylamino)methyl)-1-methyl-N-(pyridin-2-yl)-1H-benzo[d]imidazole-5-carboxamido)propanoate Hydrochloride in Anhydrous Crystalline Form 10.1 g of crude amidine (obtained in the step 1) with 101 mL of 2-propanol and 7.5 mL of water are suspended. Such suspension is heated at 75-85° C., obtaining a dissolution. It is allowed to cool and below 40° C. a solid is formed. The mixture is cooled at 0-5° C. and it is maintained for 1 hour. The solid is filtered, which is washed two times with isopropanol (4.5 mL). The solid is dried at 45° C. in a vacuum oven.

Yield: 7.22 g of the anhydrous purified crystalline form of the amidine hydrochloride salt of formula (IV-HCl); It is equivalent to 77% of theory;

Product purity: 99% measured by HPLC;

Melting point: 212° C. measured by differential scanning calorimetry technique (DSC);

X-ray diffraction peaks (angle 2-theta values (°)): 7.7; 9.7; 12.6; 15.4; 17.2; 20.2; 21.5; 25.5, and 26.5 measured on a x-ray diffractometer with Cu K alpha radiation (1.5418 Å).

Step 3: Purification and Obtaining of ethyl 3-(2-((4-carbamimidoylphenylamino)methyl)-1-methyl-N-(pyridin-2-yl)-1H-benzo[d]imidazole-5-carboxamido)propanoate hydrochloride in dihydrate crystalline Form 2.5 g of the amidine hydrochloride salt of formula (IV-HCl) from the anhydrous crystalline form obtained in the step 2 are dissolved in 10 mL of water at room temperature. Shortly after it appears abundant precipitate. This suspension is digested at 55-60° C. for 30 minutes and then the mixture is cooled at 0-5° C. and maintained for 30 minutes. The mixture is filtered and the solid dried at 50° C. 2.2 g of the amidine hydrochloride salt of formula (IV-HCl) purified in dihydrate crystalline form (KF=6.3%) are obtained.

Yield: 2.2 g of the dihydrate crystalline form of the amidine hydrochloride salt of formula (IV-HCl); 83% yield.

Product purity: 99.3% measured by HPLC.

Melting point: 212° C. measured by differential scanning calorimetry technique (DSC);

X-ray diffraction peaks (angle 2-theta values (°)): 9.7; 10.6; 12.9; 16.5; 18.0; 19.7; 20.4, and 23.5 measured on a x-ray diffractometer with Cu K alpha radiation (1.5418 Å).

The invention claimed is:

1. A process for preparing a hydrochloride salt of a compound of formula (IV-HCl)

(IV-HCl)

wherein a compound of formula (III) in free base form (III)

is reacted with hydrogen chloride in the presence of an alcohol, and then with ammonia in an aqueous medium to form an amidine hydrochloride salt of formula (IV-HCl) in the presence of water;

wherein in a step prior to the formation of the hydrochloride salt of the compound of formula (IV-HCl) is reacted a diamine of formula (II)

(II)

with carboxylic acid (I)

in the presence of a coupling reagent selected from the group consisting of N,N'-dicyclohexylcarbodiimide, N,N'-carbonyldiimidazole, and carbonyl-di-(1,2,4-triazole) and a solvent selected from the group consisting of isopropyl acetate, ethyl acetate and butyl acetate;
subsequent reaction in the presence of acetic acid to obtain a mixture; and
the mixture is heated between 75° C. and 130° C. to prepare the compound of formula (III)

2. The process according to claim 1, where the reaction is carried out in ethanol at room temperature.

3. The process according to claim 1, wherein after the reaction with hydrogen chloride, ethanol is added, and then a dissolution of aqueous ammonia up to a pH value between 8.5 and 9.5.

4. The process according to claim 1, characterized in that after neutralization of the excess of hydrogen chloride with ammonia, from 130 to 540 equivalents of water are added, and the hydrochloride salt of formula (IV-HCl) is isolated, precipitated in water by filtration.

5. The process according to claim 1, characterize in that it further comprises a subsequent purification step of the hydrochloride salt of formula (IV-HCl) by recrystallization in an isopropanol/water mixture.

6. The process according to claim 5, wherein the proportion by volume of isopropanol/water is comprised between 11:1 and 16:1.

7. The process according to claim 1, characterized in that it further comprises a purification step of the hydrochloride salt of formula (IV-HCl) by recrystallization in water.

8. The process according to claim 1, wherein the solvent is isopropyl acetate.

9. The process according to claim 1, wherein from 3 to 9 equivalents of acetic acid are added with regard to the carboxylic acid (I).

10. The process according to claim 1, wherein after the reaction of preparation of the compound (III), the compound (III) is purified by recrystallization in ethanol.

* * * * *